United States Patent [19]

Kramer

[11] Patent Number: 4,559,454
[45] Date of Patent: Dec. 17, 1985

[54] BUBBLE DETECTING INFUSION APPARATUS

[76] Inventor: Donald L. Kramer, P.O. Box 606, Wakarusa, Ind. 46573

[21] Appl. No.: 481,500

[22] Filed: Apr. 1, 1983

[51] Int. Cl.$^4$ .................................................. G01N 15/06
[52] U.S. Cl. .................................... 250/577; 604/122; 604/245; 128/DIG. 13
[58] Field of Search ................. 356/70, 133–137; 73/861.41, 293; 250/227, 560, 561, 573–575, 577; 604/253, 31, 123, 122, 245; 222/420; 340/608; 210/85, 86; 128/DIG. 13

[56] References Cited

U.S. PATENT DOCUMENTS

| | | | |
|---|---|---|---|
| 3,636,360 | 1/1972 | Oishi et al. | 356/134 |
| 4,246,489 | 1/1981 | Yoshida et al. | 250/577 |
| 4,286,873 | 9/1981 | Carson | 356/134 |
| 4,333,016 | 6/1982 | Bilstad et al. | 250/577 |
| 4,366,384 | 12/1982 | Jensen | 250/575 |

Primary Examiner—David C. Nelms
Attorney, Agent, or Firm—Joseph C. Schwalbach; Roger N. Coe

[57] ABSTRACT

Bubble detecting infusion apparatus for infusing a liquid from a source into a patient through the lumen of a light transmissive conduit member, which lumen has a flat wall surface portion contacted by the liquid in the lumen, the conduit member having an operative position within a yoke in which it is removable disposed, the yoke having a light source for directing a light beam through the conduit member wall toward the flat lumen wall surface portion thereof and having a light sensor positioned to receive light from the source reflected through the conduit member wall by the flat lumen wall surface portion, the angularity between the incident light beam and the normal to the flat lumen wall surface portion being such that when a gas bubble is in contact with the lumen flat wall surface portion, substantially all light from the source incident thereon is reflected by said surface portion toward the light sensor, and when a bubble-free liquid is in contact with the lumen flat wall surface portion, said surface portion is not substantially reflective. Shoulder means on the yoke and conduit member cooperate, when the conduit member is in operative position, to prevent rotation of the conduit member and thereby to maintain the desired angularity of the flat lumen wall surface portion with respect to the light source and the light sensor.

6 Claims, 2 Drawing Figures

BUBBLE DETECTING INFUSION APPARATUS

BACKGROUND OF THE INVENTION

This invention relates to sensing the presence of bubbles in a liquid, and a particular application thereof is the detection of air bubbles in serum or blood during infusion thereof into a patient. In such procedures it is important to insure that gas be prevented from being infused with the liquid, since air emboli can be extremely dangerous in a patient. To prevent gas from being infused it has become common practice to locate a bubble detector downline of the metering apparatus pump to automatically stop the apparatus should gas bubbles be detected.

Various instruments have been developed for preventing air bubbles from being infused into a patient along with a liquid, typical of which are those disclosed in U.S. Pat. Nos. 4,366,384, 4,312,341, 2,835,252, and 4,367,736. Such prior instrumentation commonly suffers from unreliable operation because of low signal level, electronic drift, and/or difficult mechanical alignment.

SUMMARY OF THE INVENTION

In accordance with the invention, it has bee found that the disadvantages of prior art devices can be overcome by using a single light source and single light sensor located on adjacent faces of a conduit the outside cross section of which is approximately square, with the cross section of the lumen of the conduit being in the form of a semi-circle. Due to the phenomenon of total internal reflection, semi-monochromatic light striking the diameter surface of the aforementioned semi-circle will be reflected by the surface if air is in contact therewith. If there is, however, a liquid in contact with the diameter surface, the index of refraction of which is significantly different from the index of refraction of air, the diameter surface becomes transparent, and semi-monochromatic light striking the surface will pass through the surface into the solution where it will be transmitted out through the opposite side of the conduit or be absorbed by the fluid. The net result is that the light sensor will be fully illuminated by the source if an air bubble is in contact with the lumen diameter surface, and unilluminated if a bubble-free liquid is in contact with said surface.

The present invention avoids problems inherent in certain of the prior instruments primarily by virtue of the markedly increased signal response generated by a sensor when the presence of a bubble in the liquid being monitored is sensed thereby, and also by the noncritical optical alignment requirement of components in the system.

Other objects, features and advantages of the invention will become apparent as the description proceeds, reference being had to the accompanying drawing.

DESCRIPTION OF THE PREFERRED EMBODIMENT

Figure 1:
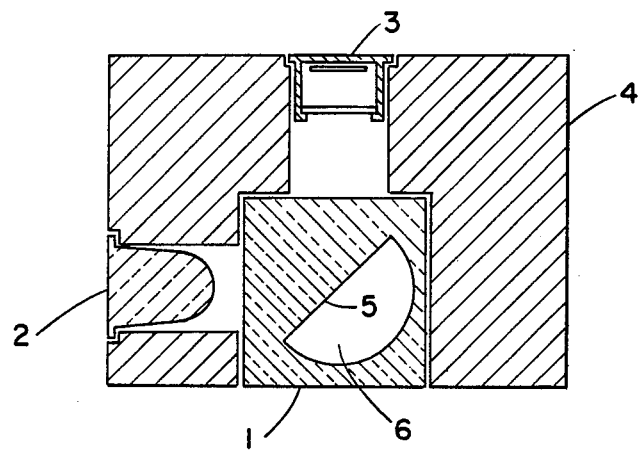
FIG. 1 is a diagrammatic illustration of the preferred form of the invention.

The inventive concept underlying the method and apparatus disclosed herein will be best understood with reference to FIG. 1. In FIG. 1 the numeral 1 indicates a tube in transverse cross-section being formed of radiation transmissive material such as glass or plastic. The tube 1 has a lumen 6 which is generally semicircular in transverse cross-section and which has a flat generally diametrical wall surface portion 5. Tube 1 is preferably incorporated in flow path means of an apparatus (not shown) for conducting an infusion liquid such as blood or serum from a source to a patient. This infused liquid is to be monitored for air bubbles as it flows from the source to the patient. The numeral 2 indicates a suitable source of radiation which emits a relatively wide light beam having a wavelength within the range of from about 300 to about 1100 nanometers; preferably a wavelength of about 665 nanometers. The source 2 preferably takes the form of a light emitting diode emitting light at approximatly 665 nanometers wavelength. Alternatively, source 2 may take the form of an incandescent lamp with which a suitable filter is used, which filter permits passage therethrough of light having a wavelength within the range of from about 300 to about 1100 nanometers; The numeral 3 indicates a radiation sensor such as a photosensor whose response characteristics are such that it responds to wavelengths of light produced by the source 2. The light source 2 and photosensor 3 are mounted in a yoke 4 which holds the conduit and restricts it from turning thereby maintaining the approximate angular relationship between the diameter surface 5 and the source 2.

Figure 2:
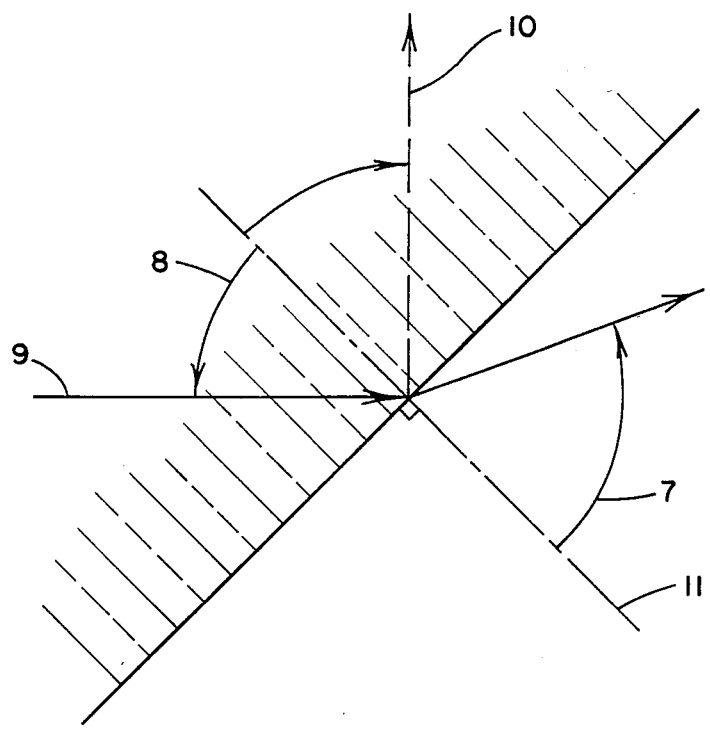
FIG. 2 is a illustration of the paths taken by light rays when traversing through a material with a high index of refraction into one with a low index of refraction.

Referring now to FIG. 2 which shows the path taken by a light ray 9 when it passes from a material (e.g. acrylic plastic) having a high index of refraction (1.5) to one (e.g. air) having a low index of refraction (1.0). In accordance with Snell's Law, as the angle of incidence 8 increases, the angle of refraction 7 also increases, but at a higher rate. When the angle of incidence 8 reaches a value such that the refracted ray 7 is at 90 degrees to the surface normal 11, that angle of incidence is a critical angle. When the angle of incidence is greater than this critical angle, the incident ray 9 is totally reflected back into the denser medium at an angle equal to the angle of incidence 8 but on the opposite side of the normal to the surface 11 as is shown by the path taken by light ray 10.

For light with a wavelength of 665 nanometers passing from a material such as acrylic plastic with an index of refraction of 1.50 to air with an index of refraction of 1.0, the critical angle is 41.8 degrees. For light with a wavelength of 665 nanometers passing from acrylic plastic to a predominantly aqueous fluid, the critical angle is 62 degrees.

Turning back now to FIG. 1, when the conduit 1 is fabricated such that the angle between the incoming semimonochromatic light from source 2 and the normal to the diameter surface 5 is greater than 42 degrees but less than 62 degrees all the light striking the diameter surface 5 will be reflected if one or more bubbles entrained in the liquid flowing through the lumen 6 contact the surface 5. If however, the liquid flowing through the lumen 6 is bubble-free, incident semi-monochromatic light will pass through the surface 5 where it will be refracted out of the system and/or be absorbed by the fluid.

Means is provided by yoke 4 to allow the conduit 1 to be easily inserted into the optical path of the apparatus, but restricted from rotating by the square cross section. By illuminating the diameter surface 5 with a wide light beam, exact front to back placement of the conduit 1 in the yoke is not required because the beam reflected from the diameter surface 5 is large, and the angular relationships between the incoming beam and the normal to the diameter surface 5 are retained.

The operation of the illustrated apparatus will now be described. With an aqueous infusion liquid to be monitored flowing through lumen 6, radiation from source 2 illuminates surface 5. Since the surface 5 is contacted by the infusion liquid, surface 5 remains essentially nonreflective so long as said liquid is bubble-free. A small portion of the impinging radiation does reflect from surface 5 and illuminates the sensor 3 the portion being approximately 2 to 6 percent of the total beam output. Hence the sensor does produce a small signal, the output being slightly above zero.

If an air bubble entrained by the infusion liquid passes through the lumen 6, it displaces the liquid in contact with the surface 5, causing it to become totally reflective. The total impinging light beam from source 2 is now reflected towards the photosensor 3 which produces a signal equal to one which would be obtained if the detector were being directly illuminated by the beam.

It will be obvious to those skilled in the art that changes in the type of light source can be made such as using an incandescent lamp with suitable optical filters to produce semimonochromatic light at any desired wavelength. It will also be obvious to those skilled in the art that by properly selecting optical wavelengths and properly selecting transmissive materials for the conduit, a bubble detector can be fashioned for any type of fluid.

Having described the invention, it will be understood that various changes and modifications may be made in the disclosed embodiment without departing from the spirit of the invention, and all of such changes are contemplated as may come within the scope of the appended claims.

What is claimed as the invention is:

1. An infusion apparatus having liquid flow path means for conducting a flowing infusion liquid from a source thereof to a patient, the improvement comprising a light transmissive conduit member in said flow path means and adapted for flow therethrough of infusion liquid, said conduit member having external shoulder means and having a lumen which is generally semicircular in transverse cross section to provide a flat generally diametrical lumen wall surface portion therein; a yoke in which said conduit member is removably disposed in operative position, said yoke having positioning shoulder means cooperable with the external shoulder means on said conduit member when the latter is in said operative position to prevent rotation of said conduit member relative to said yoke, said yoke also having a light source for directing a light beam through said conduit member wall toward said flat lumen wall surface portion when said conduit member is in said operative position, said yoke also having a light sensor positioned to receive light from said source reflected by said flat lumen wall surface portion through said conduit member wall when said conduit member is in said operative position, said yoke, when said conduit member is in said operative position therein, positioning said light source and light sensor with respect to said flat lumen wall surface portion at an angularity such that when liquid flowing through the conduit member is bubble-free, said surface is not substantially reflective, whereas when a bubble is entrained in the liquid flowing through said conduit member and contacts said flat lumen wall surface portion, substantially all of the light from said source incident upon said flat lumen wall surface portion is reflected by said wall surface portion through said conduit member wall toward said sensor, wherefore sensing of substantial light by the sensor indicates the presence of a bubble in the infusion liquid flowing through said conduit member.

2. The infusion apparatus of claim 1 wherein said conduit member has an outer surface which is polygonal in transverse cross section, and the positioning shoulder means on said yoke engages said outer surface when the conduit member is in said operative position to prevent rotation of the conduit member within the yoke.

3. The infusion apparatus of claim 1 wherein said conduit member has an outer surface which is rectangular in cross section, and the positioning shoulder means on said yoke comprises a recess which is rectangular in cross section and in which said conduit member is removably disposed when in said operative position, the rectangular cross section of said yoke recess and the outer surface of said conduit member being complemental to provide cooperable shoulder means preventing rotation of said conduit member within said yoke when the conduit member is in said operative position.

4. The infusion apparatus of claim 1 wherein said conduit member is formed of light transmissive glass or plastic.

5. The infusion apparatus of claim 1 wherein said light source is a light emitting diode which emits light at a wavelength within the range of from about 300 to about 1100 manometers.

6. The infusion apparatus of claim 1 wherein said light source is an incandescent lamp, said apparatus additionally comprising a filter positioned in the light path between said source and said sensor effective to limit the light passing therethrough to within the range of about 300 to 1100 manometers.

* * * * *